US011116770B2

(12) United States Patent
Sinclair

(10) Patent No.: US 11,116,770 B2
(45) Date of Patent: Sep. 14, 2021

(54) DETECTION AND TREATMENT OF EXCESSIVE HAIR SHEDDING

(71) Applicant: Samson Clinical Pty Ltd, Melbourne (AU)

(72) Inventor: Rodney Sinclair, East Melbourne (AU)

(73) Assignee: Samson Clinical Pty Ltd

(*) Notice: Subject to any disclaimer, the term of this patent is extended or adjusted under 35 U.S.C. 154(b) by 0 days.

(21) Appl. No.: 16/252,107

(22) Filed: Jan. 18, 2019

(65) Prior Publication Data

US 2019/0192513 A1    Jun. 27, 2019

Related U.S. Application Data

(63) Continuation of application No. 15/522,599, filed as application No. PCT/AU2015/050682 on Oct. 29, 2015, now Pat. No. 10,226,462.

(30) Foreign Application Priority Data

Oct. 29, 2014 (AU) ................................ 2014904327

(51) Int. Cl.

| A61K 31/506 | (2006.01) |
|---|---|
| A61Q 7/00 | (2006.01) |
| A61K 31/56 | (2006.01) |
| A61K 8/49 | (2006.01) |
| A61K 45/06 | (2006.01) |
| A61K 31/167 | (2006.01) |
| A61K 31/522 | (2006.01) |
| A61K 31/57 | (2006.01) |
| A61K 31/58 | (2006.01) |
| A61K 31/585 | (2006.01) |
| A61K 33/04 | (2006.01) |
| A61K 33/14 | (2006.01) |
| A61K 33/30 | (2006.01) |
| A61K 36/484 | (2006.01) |
| A61P 17/14 | (2006.01) |

(52) U.S. Cl.
CPC .......... *A61K 31/506* (2013.01); *A61K 8/4953* (2013.01); *A61K 8/4973* (2013.01); *A61K 31/167* (2013.01); *A61K 31/522* (2013.01); *A61K 31/56* (2013.01); *A61K 31/57* (2013.01); *A61K 31/58* (2013.01); *A61K 31/585* (2013.01); *A61K 33/04* (2013.01); *A61K 33/14* (2013.01); *A61K 33/30* (2013.01); *A61K 36/484* (2013.01); *A61K 45/06* (2013.01); *A61P 17/14* (2018.01); *A61Q 7/00* (2013.01)

(58) Field of Classification Search
CPC .. A61K 31/506; A61K 31/167; A61K 31/522; A61K 31/56; A61K 31/57; A61K 31/58; A61K 31/585; A61K 8/4953; A61K 8/4973; A61K 33/04; A61K 33/14; A61K 33/30; A61K 36/484; A61K 45/06; A61P 45/06; A61Q 7/00

See application file for complete search history.

(56) References Cited

U.S. PATENT DOCUMENTS

| 4,997,643 A | 3/1991 | Partain, III et al. |
|---|---|---|
| 5,373,012 A * | 12/1994 | Schostarez ................ A61P 9/12 |
| | | 514/275 |
| 6,136,860 A | 10/2000 | Rushton |
| 9,561,224 B1 | 2/2017 | Rogosnitzky |
| 10,226,462 B2 | 3/2019 | Sinclair |
| 2007/0166362 A1 | 7/2007 | Sakuma et al. |
| 2008/0064765 A1 | 3/2008 | Birnbaum |
| 2008/0187588 A1* | 8/2008 | Zuleger ................ A61K 9/0004 |
| | | 424/469 |
| 2019/0269684 A1 | 9/2019 | Sinclair |

FOREIGN PATENT DOCUMENTS

| AU | 2011/100917 | * | 9/2011 |
|---|---|---|---|
| AU | 2011100917 | | 9/2011 |
| JP | 2000038340 | | 2/2000 |
| JP | 2003012542 | | 1/2003 |
| WO | 1994018936 | | 9/1994 |
| WO | WO1999040898 | | 8/1999 |
| WO | WO2007023396 | | 3/2007 |
| WO | WO 2008/067158 | * | 6/2008 |
| WO | WO2008067158 | | 6/2008 |
| WO | 2010036947 | | 4/2010 |
| WO | WO2012140252 | | 10/2012 |
| WO | WO2013181487 | | 12/2013 |
| WO | WO2016065426 | | 5/2016 |

OTHER PUBLICATIONS

Fiedler-Weiss et al. Arch Dermatol, 1987, vol. 123, 1488-1490.*
Pratt, C. Herbert, et al., (2017) "Alopecia areata", Nat Rev Dis Primers, 3:1-37.
Hadshiew, Ina M., et al., (2004) "Burden of Hair Loss: Stress and the Underestimated Psychosocial Impact of Telogen Effluvium and Androgenetic Alopecia", J Invest Dermatol, 123:455-457.
Fiedler-Weiss, Virginia C., (1987) "Evaluation of Oral Minoxidil in the Treatment of Alopecia Areata", Archives of Dermatology, 123(11): 1488.
Tsuboi, Ryoji, (2009) "Current status and future prospects of male pattern baldness treatment", Nippon Pharmacology (Folia Pharmacol Jpn.), 133:78-81.
Perera, Eshini and Sinclair, Rodney, (2017) "Treatment of chronic telogen effluvium with oral minoxidil: A retrospective study", F1000Research, 6:1650, 6 pages.
Arck et al. (2003) "Topical minoxidil counteracts stress-induced hair growth inhibition in mice", Exp Dermatol, 12(5):580-90.
Extended European Search Report for EP Application No. 15854489.0, dated Jun. 4, 2018, 9 pages.

(Continued)

*Primary Examiner* — Genevieve S Alley
(74) *Attorney, Agent, or Firm* — Carol L. Francis; Bozicevic, Field & Francis LLP

(57) ABSTRACT

The present invention relates to a method of treating or preventing hair loss or excessive hair shedding in a subject by administering to a subject an oral dose of minoxidil. In particular, the present invention relates to a method of treating telogen effluvium in a subject by administering to a subject an oral dose of minoxidil.

25 Claims, 10 Drawing Sheets

(56) References Cited

OTHER PUBLICATIONS

Fiedler, V C et al., (1987) "Immunohistochemical characterization of the cellular infiltrate in severe alopecia areata before and after minoxidil treatment", Dermatologica, 175(2):29-35.
Garcia-Hernandez, et aL, (1999) "Chronic Telogen Effluvium: Incidence, Clinical and Biomechanical Features, and Treatment", Arch Dermatol, 135:1123-1124.
Hordinsky, Maria K., (2006) "Medical Treatment of Noncicatricial Alopecia", Semin Cutan Med Surg, 25:51-55.
PCT International Search Report for PCT application serial No. PCT/AU2015/050682, dated Nov. 24, 2015,4 pages.
Hadshiew et al., (2004) "Burden of Hair Loss: Stress and the Underestimated Psychosocial Impact of Telogen Effluvium and Androgenetic Alopecia", J Invest Dermatol, 123:455-457.
Fiedler, Virgina C., (1988) "Direct T-Cell Effects of Minoxidil", Clinics in Dermatology, 6(4):148-151.
Buhl et al., (1989) "Minoxidil stimulates mouse vibrissae follicles in organ culture.", J Invest Dermatol, 92(3):315-20.
Fleishaker et al., (1989) "The Pharmacokinetics of 2.5-to 10-mg Oral Doses of Minoxidil in Healthy Volunteers.", Journal of Clinical Pharma, 29:162-167.
Kaur, (2013) "Dissertation regarding Sublingual Drug Delivery", In Vitro-In Vivo Correlation, 1-24.
Shorter et al., (2008) "Human hair follicles contain two forms of ATP-sensitive potassium channels, only one of which sensitive to Minoxidil.", The FASEB Journal, 22:1725-1736.
Ramos el al., (2020) "Oral minoxidil bio-activation by hair follicle outer root sheath cell sulfotransferase enzymes predicts clinical efficacy in female pattern hair loss", Journal of the European Academy of Dermatology and Venereology, 34(1):e40-e41.
Wambier et al., (2019) "Combination tofacitinib and oral minoxidil treatment for severe alopecia areata", Journal of the American Academy of Dermatology, 1-8.
Meidan, Victor, M., and Touitou, Elka, (2001) "Treatments for Androgenetic Alopecia and Alopecia Areata", Drugs, 61(1):53-69.
Fiedler-Weiss, Virginia C., (1987) "Potential mechanisms of minoxidil-induced hair growth in alopecia areata", Journal of the American Academy of Dennatology, 16(3):653-656.
Meisheri, Kaushik, et al., (1993) "Enzymatic and Non-Enzymatic Sulfation Mechanisms in the Biological Actions of Minoxidil", Biochemical Pharmacology, 45(2):271-279.
Leonard-Segal, Andrea, NDA 21-812, Minoxidil, Men's Rogaine Extra Strength 5% Topical Foam, Center for Drug Evaluation and Research, Application No. 21-812, Medical Review, Jan. 18, 2006, pp. 1-123.
Cranwell. W. C., et al., (2018) "Treatment of alopecia areata: An Australian expert consensus statement", Australas J Dermatol, 60:163-170.
Kurosawa M, et al., (2006) "A comparison of the efficacy, relapse rate and side effects among three modalities of systematic corticosteroid therapy for alopecia areata", Dermatology, 212(4):361-5.

* cited by examiner

Patient 1

Patient 2

Patient 3

Patient 4

Patient 5

Patient 6

Patient 7

Patient 10

Patient 11

Patient 12

Patient 13

Patient 14

Patient 15

DETECTION AND TREATMENT OF EXCESSIVE HAIR SHEDDING

TECHNICAL FIELD

The present invention relates to detection and treatment of hair loss or excessive hair shedding. In one aspect, the present invention relates to treatment of telogen effluvium. The present invention also relates to a visual analogue scale for determining hair loss or excessive hair shedding.

BACKGROUND

Hair follicles on the scalp do not continuously produce hair. They cycle through a growth stage that can last two or more years, then regress to a resting stage for up to two months before starting to grow a new hair fiber again. At any time on a healthy human scalp, about 80% to 90% of the hair follicles are growing hair. These active follicles are in what is called the anagen phase. That leaves up to 10% to 20% percent of scalp hair follicles in a resting state called telogen, when they don't produce any hair fiber. Changes in actual amount of hair fall occur in number of hair loss conditions including anagen effluvium, acute and chronic telogen effluvium, alopecia areata, cicatricial alopecia, male pattern hair loss (MPHL) and female pattern hair loss (FPHL).

Men commonly complain of increased hair loss or hair shedding, especially after washing their hair. Changes in actual amount of hair fall occur in number of hair loss conditions including anagen effluvium, acute and chronic telogen effluvium, alopecia areata, cicatricial alopecia and male pattern hair loss (MPHL).

Female pattern hair loss (FPHL) is the most common cause of hair loss encountered in clinical practice for women (Messenger et al. 2010). FPHL is a complex polygenic disorder characterised clinically by diffuse hair thinning over the mid frontal scalp and histologically by hair follicle miniaturization. The proportion of miniaturized follicles increases with the severity of hair loss (Messenger et al. 2006). FPHL adversely impacts quality of life and the prevalence of FPHL increases with age. In a population study of over 700 women, FPHL was found in 12% of women aged 20-29 and 57% of women aged >80. Hair loss severity also increases with age.

One such condition that results in in increased hair loss or excessive hair shedding is telogen effluvium (TE). This condition effects both men and women, occurring more commonly in women. TE is a non-scarring alopecia characterised by excessive shedding of telogen club hair diffusely from the scalp. It generally begins 8-12 weeks after a triggering event such as pregnancy, major illness or complicated surgery and is resolves within 3-6 months. Once resolved, self-limiting telogen effluvium can be retrospectively diagnosed as acute telogen effluvium (Harrison S and Sinclair R, 2002). Telogen shedding that persists beyond 6 months is called chronic telogen effluvium (CTE) (Whiting, D A 1996). CTE may be primary or secondary to a range of triggers including androgenetic alopecia (AGA), nutritional deficiency, endocrinopathy, connective tissue disease or drug induced (Messenger et al., 2010).

The aetiology of primary CTE is unknown (Whiting, D A 1996). The natural history is for continued hair shedding over many years. Long-term follow up studies of women with primary CTE (Bittencourt C, 2014) and histomorphometric and immunohistochemical examination of scalp biopsies in patients with both FPHL and CTE have confirmed that primary CTE is not a prodrome to AGA (Whiting D A, 1996).

Primary CTE most commonly occurs suddenly in females between 30 and 50 years of age. Additional clinical features commonly seen in primary CTE include bi-temporal recession of the anterior hairline, a reduction in the thickness of their ponytail diameter (Whiting, D A 1996) and trichodynia (Kivanç-Altunay, İ. et al. 2003). Widening of the central part line suggests AGA and is not a feature of primary CTE. Other than identification and treatment of a triggering event such as hypothyroidism, there is no known treatment for acute telogen effluvium (ATE) or CTE (Garcia-Hernandez M J et al. 1999). Treatments commonly used for AGA such as finasteride, cyproterone acetate, spironolactone and flutamide do not work in TE (Messenger A et al. 2010). Currently, the only suggested treatment for CTE is topical minoxidil, however results are variable and often disappointing. One study demonstrated an improvement in 55.2% of patients studied, using 5% topical minoxidil for men and 5% topical minoxidil with 50 mg of cyproterone acetate for women (Garcia-Hernandez et al. 1999). Only 25.2% of patients had a moderate response to treatment (Garcia-Hernandez et al. 1999). There are currently no FDA or TGA treatments available for chronic telogen effluvium.

There is a requirement for new treatments for conditions of hair loss and excessive hair shedding for both men and women, including telogen effluvium. There is also a requirement for rapid, inexpensive and simple tools for monitoring excessive hair shedding.

SUMMARY

Research described herein has led to the unexpected finding that hair loss or excessive hair shedding can be effectively treated by a daily low dose of oral minoxidil. Related research has also led to the unexpected finding that telogen effluvium, a scalp disorder characterized by the thinning or shedding of hair resulting from the early entry of hair in the telogen phase (the resting phase of the hair follicle), can be treated with oral minoxidil. Further, it has been found that administration of a pharmaceutical salt concentration with oral minoxidil has a an advantageous effect on blood pressure. Further, a novel visual analogue scale for assessment of hair loss or hair shedding has been developed. This scale defines normal hair shedding as well as the range of hair shedding seen in female pattern hair loss (FPHL) and therefore enables diagnosis of women who have hair loss or excess hair shedding. This visual analogue scale has facilitated the assessment of hair shedding in normal conditions and conditions of hair loss.

In one aspect, the present disclosure provides a method of treating or preventing excessive hair loss or hair shedding in a subject by administering to a subject an oral dose of minoxidil within the range from about 0.1 mg to 0.49 mg, or from about 0.1 mg to 0.4 mg, or from about 0.15 mg to 0.3 mg, or from about 0.2 mg to 0.28 mg, or is about 0.25 mg, or is about 0.24 mg, or is about 0.1 mg daily. In one example, the oral minoxidil dose is about 0.25 mg daily. In one example, the oral minoxidil is about 0.24 mg daily. In one example. The oral minoxidil is about 0.1 mg daily.

In one example, the method further comprises administering spironolactone within the range of from about 10 mg to 500 mg, or from about 10 mg to 400 mg, or from about 10 mg to 300 mg, or from about 15 mg to 200 mg, or form about 15 mg to 150 mg, or from about 18 mg to 100 mg, or from about 20 mg to 80 mg, or from about 20 mg to 50 mg, or from about 22 mg to 40 mg, or from about 23 mg to 35 mg, or from about 23 mg to 30 mg. In one example, spironolactone is administered at a concentration of about 25 mg.

In one example, the method further comprises administering a pharmaceutical dose of salt. In one example, the pharmaceutical dose of salt can be sodium chloride. In one example, the method further comprises administering sodium chloride with the range of from about 10 mg to 200 mg, from about 15 mg to 150 mg, from about 15 mg to 125 mg, from about 20 mg to 100 mg, from about 25 mg to 80 mg, from about 30 mg to 70 mg, from about 40 mg to 60 mg, from about 45 mg to 55 mg. In one example, sodium chloride is administered at a concentration of at least 10 mg, or at least 15 mg, or at least 20 mg, or at least 25 mg, or at least 30 mg, or at least 35 mg, or at least 40 mg, or at least 45 mg, or at least 50 mg, or at least 100 mg, or at least 200 mg. In one example, sodium chloride is administered at a concentration of about 50 mg. In one example, sodium chloride is administered at a concentration of about 20 mg.

In one example, the method further comprises an excipient. In one example, the excipient is selected from one or more of: starch, corn starch, colloidal silicon dioxide, lactose, magnesium stearate, microcrystalline cellulose, anhydrous lactose, docusate sodium, magnesium stearate, microcrystalline cellulose, sodium benzoate and sodium starch glycolate.

In one example, the method further comprises administering zinc. In one example, the method further comprises administering zinc within the range of from about 0.1 mg to 100 mg, or from about 0.1 mg to 75 mg, or from about 0.1 mg to 50 mg, from about 0.1 mg to 20 mg, from about 1 mg to 15 mg, from about 2.5 mg to 15 mg, from about 5 mg to 13 mg, from about 8 mg to 12 mg, from about 10 mg to 12 mg daily. In one example, the zinc concentration is about 5 mg daily. In one example, the zinc concentration is about 8 mg daily. In one example, the zinc concentration is about 12 mg daily.

In one example, the method further comprises administering selenium. In one example, the method further comprises administering selenium within the range of from about 10 µg to 200 µg, from about 15 µg to 150 µg, from about 15 µg to 125 µg, from about 20 µg to 100 µg, from about 25 µg to 80 µg, from about 30 µg to 70 µg, from about 40 µg to 60 µg, from about 45 µg to 55 µg daily. In one example, selenium is administered at a concentration of about 50 µg daily. In one example, selenium is administered at a concentration of about 20 µg daily.

In one example, the method further comprises administering caffeine. In one example, the method further comprises administering caffeine within the range of from about 50 mg to 250 mg, from about 60 mg to 240 mg, from about 80 mg to 220 mg, from about 100 mg to 200 mg, from about 100 mg to 150 mg daily.

In one example, the method further comprises administering liquorice. In one example, the method further comprises administering liquorice within the range of from about 50 mg to 250 mg, from about 60 mg to 240 mg, from about 80 mg to 220 mg, from about 100 mg to 200 mg, from about 100 mg to 150 mg daily.

In one example, the method further comprises administering a vitamin, wherein the vitamin is selection from: vitamin A, vitamin B, vitamin C and vitamin D.

In one example, the method further comprises administering an amino acid, wherein the amino acid is selected from tyrosine, methionine, thymine, arginine, cysteine, lysine and cysteine.

In one example, the method additionally comprises administering an antiandrogen.

In one example, the method additionally comprises administering one or more of: (i) finasteride within the range of from about 0.1 mg to 1 mg; (ii) dutasteride within the range of from about 0.01 mg to 1 mg; (iii) flutamide within the range of from about 10 mg to 500 mg; (iv) cyproterone acetate within the rage of from about 1 mg to 100 mg; (v) bicalutamide within the range of from about 1 mg to 100 mg; (vi) enzalutamide within the range of from about 1 mg to 100 mg; (vii) nilutamide within the range of from about 1 mg to 100 mg; (xiii) drosperidone within the range of from about 0.1 mg to 10 mg; (ix) apalutamide within the range of from about 1 mg to 100 mg; and/or (x) buseralin within the range of from about 0.1 mg to 10 mg.

In one example, the present disclosure further provides a composition when used to treat hair loss or excessive hair shedding via oral administration comprising; (i) minoxidil within the range of from about 0.1 mg to 0.49 mg; (ii) minoxidil at a concentration of about 0.1 mg; (iii) minoxidil at a concentration of about 0.24 mg; (iv) minoxidil at a concentration of about 0.25 mg; (v) minoxidil within the range of from about 0.1 mg to 0.49 mg and spironolactone within the range of from about 10 mg to 500 mg; or (vi) minoxidil at a concentration of about 0.25 mg and spironolactone at a concentration of about 25 mg.

In one example, the composition additionally comprises: (i) sodium chloride at a concentration of from about 10 to 200 mg; (ii) sodium chloride at a concentration from about 50 mg; or (iii) sodium chloride at a concentration from about 20 mg.

In one example, the composition additionally comprises one or more of: (i) finasteride within the range of from about 0.1 mg to 1 mg; (ii) dutasteride within the range of from about 0.01 mg to 1 mg; (iii) flutamide within the range of from about 10 mg to 500 mg; (iv) spironolactone within the range of from about 10 mg to 500 mg; (v) cyproterone acetate within the rage of from about 1 mg to 100 mg; (vi) bicalutamide within the range of from about 1 mg to 500 mg; (vii) enzalutamide within the range of from about 1 mg to 100 mg; (viii) nilutamide within the range of from about 1 mg to 100 mg; (ix) drosperidone within the range of from about 0.1 mg to 10 mg; (x) apalutamide within the range of from about 1 mg to 100 mg; and/or (xi) buseralin within the range of from about 0.1 mg to 10 mg.

In one example, the composition further comprises an excipient. In one example, the excipient is selected from one or more of: starch, corn starch, colloidal silicon dioxide, lactose, magnesium stearate, microcrystalline cellulose, anhydrous lactose, docusate sodium, magnesium stearate, microcrystalline cellulose, sodium benzoate and sodium starch glycolate.

In one example, the composition of the present disclosure is in the form of a capsule. In one example, the composition of the present disclosure is in the form of a tablet.

In one example, the present disclosure provides use of about 0.25 mg minoxidil for the preparation of a medicament for the treatment of hair loss or excessive hair shedding in a subject. In one example, the medicament additionally comprises one or more of: (i) spironolactone within the range of from about 10 mg to 500 mg; or (ii) finasteride within the range of from about 0.1 mg to 1 mg; (iii) dutasteride within the range of from about 0.01 mg to 1 mg; (iv) flutamide within the range of from about 10 mg to 500 mg; (v) cyproterone acetate within the rage of from about 1 mg to 100 mg; (vi) bicalutamide within the range of from about 1 mg to 100 mg; (vii) enzalutamide within the range of from about 1 mg to 100 mg; (viii) nilutamide within the range of from about 1 mg to 100 mg; (ix) drosperidone within the range of from about 0.1 mg to 10 mg; (x) apalutamide within the range of from about 1 mg to 100 mg; and/or (xi) buseralin within the range of from about 0.1 mg to 10 mg.

In one example, the subject is female. In one example the subject is male.

In one aspect, the present invention provides a method of treating telogen effluvium by administering to a subject an oral dose of minoxidil within the range from about 0.1 mg to 20 mg, or from about 0.1 mg to 15 mg, or from about 0.1 mg to 10 mg, or from about 0.1 mg to 5 mg, or from about 0.1 mg to 3 mg, or from about 0.1 mg to 2.5 mg, or from about 0.1 mg to 2 mg, or from about 0.1 mg to 1.5 mg, or from about 0.1 mg to 1 mg, or from about 0.1 mg to 0.75 mg, or from 0.1 to 0.5 mg, or from about 0.1 to 0.25 mg daily. In one example, the telogen effluvium is chronic telogen effluvium.

In one example, the oral minoxidil dose is about 25 mg, or is about 20 mg, or is about 15 mg, or is about 10 mg, or is about 5 mg, or is about 3 mg, or is about 2.5 mg, or is about 2 mg, or is about 1.5 mg, or is about 1 mg, or is about 0.75 mg, or is about 0.5 mg, or is about 0.49 mg, or is about 0.48 mg, or is about 0.25 mg, or is about 0.24 mg, or is about 0.1 mg daily. In one example, the oral minoxidil dose is about 2.5 mg daily. In one example, the oral minoxidil dose is about 1 mg daily. In one example, the oral minoxidil dose is about 0.5 mg daily. In one example, the oral minoxidil dose is about 0.25 mg daily. In one example, the oral minoxidil dose is about 0.24 mg daily. In one example, the oral minoxidil dose is about 0.1 mg daily.

In one example, the method further comprises administering a: aldosterone antagonist, 5α-reductase inhibitor, non-steroidal antiandrogen drug and/or a steroidal antiandrogen.

In one example, the method further comprises administering spironolactone within the range of from about 10 mg to 500 mg, or from about 10 mg to 400 mg, or from about 10 mg to 300 mg, or from about 15 mg to 200 mg, or form about 15 mg to 150 mg, or from about 18 mg to 100 mg, or from about 20 mg to 80 mg, or from about 20 mg to 50 mg, or from about 22 mg to 40 mg, or from about 23 mg to 35 mg, or from about 23 mg to 30 mg, or is about 25 mg. In one example, spironolactone is at a concentration of about 25 mg.

In one example, the method further comprises administering sodium chloride with the range of from about 10 mg to 200 mg, from about 15 mg to 150 mg, from about 15 mg to 125 mg, from about 20 mg to 100 mg, from about 25 mg to 80 mg, from about 30 mg to 70 mg, from about 40 mg to 60 mg, from about 45 mg to 55 mg. In one example, sodium chloride at a concentration of about 50 mg. In one example, sodium chloride at a concentration of about 20 mg.

In one example, the method additionally comprises administering one or more of:
 (i) finasteride within the range of from about 0.1 mg to 1 mg;
 (ii) dutasteride within the range of from about 0.01 mg to 1 mg;
 (iii) flutamide within the range of from about 10 mg to 500 mg;
 (iv) cyproterone acetate within the rage of from about 1 mg to 100 mg;
 (v) bicalutamide within the range of from about 1 mg to 100 mg;
 (vi) enzalutamide within the range of from about 1 mg to 100 mg;
 (vii) nilutamide within the range of from about 1 mg to 100 mg;
 (viii) drosperidone within the range of from about 0.1 mg to 10 mg;
 (ix) apalutamide within the range of from about 1 mg to 100 mg; and/or (x) buseralin within the range of from about 0.1 mg to 10 mg.

In an aspect, the present invention also provides a composition when used to treat telogen effluvium via oral administration comprising;
 (i) minoxidil within the range of from about 0.1 mg to 20 mg;
 (ii) minoxidil at a concentration of about 0.1 mg;
 (iii) minoxidil at a concentration of about 0.24 mg;
 (iv) minoxidil at a concentration of about 0.25 mg;
 (v) minoxidil at a concentration of about 0.5 mg;
 (vi) minoxidil within the range of from about 0.1 mg to 20 mg and spironolactone within the range of from about 10 mg to 500 mg;
 (vii) minoxidil at a concentration of about 0.25 mg and spironolactone at a concentration of about 25 mg.

In one example, the composition additionally comprises one or more of:
 (i) sodium chloride at a concentration of from about 10 to 200 mg;
 (ii) sodium chloride at a concentration of about 50 mg;
 (iii) zinc at a concentration of about 0.1 to 20 mg;
 (iv) zinc at a concentration of about 8 mg;
 (v) selenium at a concentration of 20 μg to 200 μg;
 (vi) caffeine at a concentration of about 50 mg to 250 mg;
 (vii) liquorice at a concentration of about 50 mg to 250 mg;
 (viii) at least one vitamin; and/or
 (ix) at least one amino acid.

In one example, the composition additionally comprises one or more of:
 (i) finasteride within the range of from about 0.1 mg to 1 mg;
 (ii) dutasteride within the range of from about 0.01 mg to 1 mg;
 (iii) flutamide within the range of from about 10 mg to 500 mg;
 (iv) spironolactone within the range of from about 10 mg to 500 mg;
 (v) cyproterone acetate within the rage of from about 1 mg to 100 mg;
 (vi) bicalutamide within the range of from about 1 mg to 100 mg;
 (vii) enzalutamide within the range of from about 1 mg to 100 mg;
 (viii) nilutamide within the range of from about 1 mg to 100 mg;
 (ix) drosperidone within the range of from about 0.1 mg to 10 mg;
 (x) apalutamide within the range of from about 1 mg to 100 mg; and/or
 (xi) buseralin within the range of from about 0.1 mg to 10 mg.

In one example, the composition as herein described is in the form of a capsule. In one example, the composition as herein described is in the form of a tablet.

In an aspect, the present invention provides use of about 2.5 mg minoxidil for the preparation of a medicament for the treatment of telogen effluvium in a subject.

In an aspect, the present invention provides use of about 1 mg minoxidil for the preparation of a medicament for the treatment of telogen effluvium in a subject.

In an aspect, the present invention provides use of about 0.5 mg minoxidil for the preparation of a medicament for the treatment of telogen effluvium in a subject.

The present disclosure also provides a visual analogue scale for assessment of hair loss or excessive hair shedding comprising a plurality of images, wherein each image is representative of a level of daily hair shedding.

In one example, at least one image is representative of a normal level of daily hair shedding. In one example, at least one image is representative of an excessive level of daily hair shedding.

For example, each image may be of a bundle of hair. The bundle of hair may comprise short hairs, shoulder length hairs or long hairs. In one example, the bundle of hair comprises shoulder length or long hairs.

In one example, the bundle of hair comprises hairs that are a shade of black, brown, blond, red or grey. In one example the visual analogue scale is tailored to the subjects length and/or colour of hair.

In one example, a visual analogue scale comprises at least one or more of: (i) an image of a bundle of about 5 to 25 hairs; (ii) an image of a bundle of about 25 to 75 hairs; (iii) an image of a bundle of about 75 to 150 hairs; (iv) an image of a bundle of about 150 to 200 hairs; (v) an image of a bundle of about 200 to 250 hairs; (vi) an image of a bundle of about 250 to 300 hairs; (vii) an image of a bundle of about 300 to 350 hairs; (viii) an image of a bundle of about 350 to 400 hairs; (ix) an image of a bundle of about 400 to 450 hairs; (x) an image of a bundle of about 450 to 500 hairs; (xi) an image of a bundle of about 500 to 550 hairs; (xii) an image of a bundle of about 550 to 600 hairs; (xiii) an image of a bundle of about 600 to 650 hairs; (xiv) an image of a bundle of about 650 to 700 hairs; (xv) an image of a bundle of about 700 to 750 hairs; (xvi) an image of a bundle of about 750 to 800 hairs; (xvii) an image of a bundle of about 800 to 850 hairs; (xviii) an image of a bundle of about 850 to 900 hairs; (xix) an image of a bundle of about 900 to 950 hairs; (xx) an image of a bundle of about 950 to 1000 hairs In one example, a visual analogue scale comprises: (i) an image of a bundle of about 5 to hairs 25; (ii) an image of a bundle of about 25 to hairs 75; (iii) an image of a bundle of about 75 to 150 hairs; (iv) an image of a bundle of about 100 to 300 hairs; (v) an image of a bundle of about 200 to 500 hairs; (vi) an image of a bundle of about 250 to 750 hairs.

In one example, a visual analogue scale comprises: (i) an image of a bundle of about 5 to hairs 25; (ii) an image of a bundle of about 25 to hairs 75; (iii) an image of a bundle of about 75 to 150 hairs; (iv) an image of a bundle of about 150 to 300 hairs; (v) an image of a bundle of about 300 to 500 hairs; (vi) an image of a bundle of about 500 to 1000 hairs.

In one example, the present disclosure provides a visual analogue scale wherein the images are photographic images. In one example, the present disclosure provides a visual analogue scale wherein images are displayed on a single page or on a screen. In one example, the present disclosure provides a visual analogue scale wherein the images are displayed on a separate page or on a screen. In one example, the images are numbered. The page may be, for example, an A4 page.

In one example, the present disclosure provides a method of diagnosing or monitoring a condition characterized by hair loss or excessive hair shedding in a subject, or monitoring treatment of a condition characterized by hair loss or excessive hair shedding in a subject, the method comprising determining the level of daily hair shedding by using a visual analogue scale of the present disclosure. In on example, the condition characterized by hair loss or excessive hair shedding is one of alopecia areata, androgenetic alopecia, telogen effluvium (chronic and acute), anagen effluvium, male pattern baldness, female pattern baldness, thyroid problems, monilethrix, anaemia, cicatricial alopecia (lichen planopilaris, discoid lupus erythematosus, folliculitis decalvans), congenital hypotrichosis, polycystic ovary syndrome or malnutrition. In one example, the condition is androgenic alopecia. In one example, the condition is telogen effluvium. In one example, the condition is chronic telogen effluvium. In one example, the condition is acute telogen effluvium. In one example, the condition is androgenic alopecia. In one example, the subject is female.

In one example, the subject may use the visual analogue scale after hair is washed. In one example, a subject may use the visual analogue scale before hair is washed. In one example, the subject may additionally record hair washing events.

In one example, a subject indicates how much hair is shed in a single day by selecting an image from the visual analogue scale, wherein the image selected indicates the amount of hair shed on any given day. In one example, a subject indicates how much hair they shed on an average day by selecting an image from the visual analogue scale, wherein the image selected indicates the amount of hair shed. In one example, the visual analogue scale is used daily or weekly for the assessment of hair loss or hair shedding.

In one example, the scale comprises six images. In one example, four images correspond with normal levels of hair shedding and two images correspond with excessive levels of hair shedding.

For example, normal levels of hair shedding may be represented by one or more of (i) an image of a bundle of about 5 to 25 hairs; (ii) an image of a bundle of about 25 to 75 hairs; (iii) an image of a bundle of about 75 to 150 hairs.

For example, excessive levels of hair shedding may be represented by (i) an image of a bundle of about 300 to 750 hairs and/or (ii) an image of a bundle of about 500 to 1000 hairs.

In one example, the method additionally comprises monitoring one or more or all of: (i) daily hair shedding over time, (ii) daily hair shedding in response to a treatment; (iii) daily hair shedding in response to a hair loss or excessive hair shedding treatment; (iv) daily hair shedding in response to treatment as described herein.

In one example, the present disclosure provides the use of the visual analogue scale according to any one of claims for detecting a normal or an excessive level of daily hair shedding.

As described herein according to any example minoxidil may be additionally administered with one or more other treatments for hair loss or excessive hair shedding. In one example, other treatments for hair loss or excessive hair shedding include treatments which are administered orally, intravenously and topically. In one example, minoxidil is additionally administered with an oral antiandrogen. Exemplary treatments include: finasteride (propecia), dutasteride (avodart), flutamide, spironolactone (aldactone), cimetidine (tagamet), cyproterone acetate, bicalutamide, enzalutamide, nilutamide, apalutamide, buserelin, trans retinoic acid, oral contraceptives such as low dose androgen index birth control pills, estrogen and/or progesterone.

As described herein according to any example, the subject has a condition characterized by hair loss or excessive hair shedding. As described herein according to any example, the subject has a condition characterized by hair follicle miniaturization. As described herein according to any example, the hair loss or excessive hair shedding is the result of a genetic condition. As described herein according to any example, the hair loss or excessive hair shedding is the result of environmental factors. Exemplary conditions include alopecia areata, androgenetic alopecia, telogen effluvium, anagen effluvium (associated which chemotherapy), male pattern baldness, female pattern baldness, monilethrix, thyroid problems (e.g. disease characterized by hypothyroidism and hyperthyroidism), scale infections, anaemia, polycystic ovary syndrome and malnutrition. In one example, the condition is androgenic alopecia.

As described herein according to any example the subject is a mammal. As described herein according to any example the subject is human. As described herein according to any example the subject is female.

DESCRIPTION OF EMBODIMENTS

Figure 1:
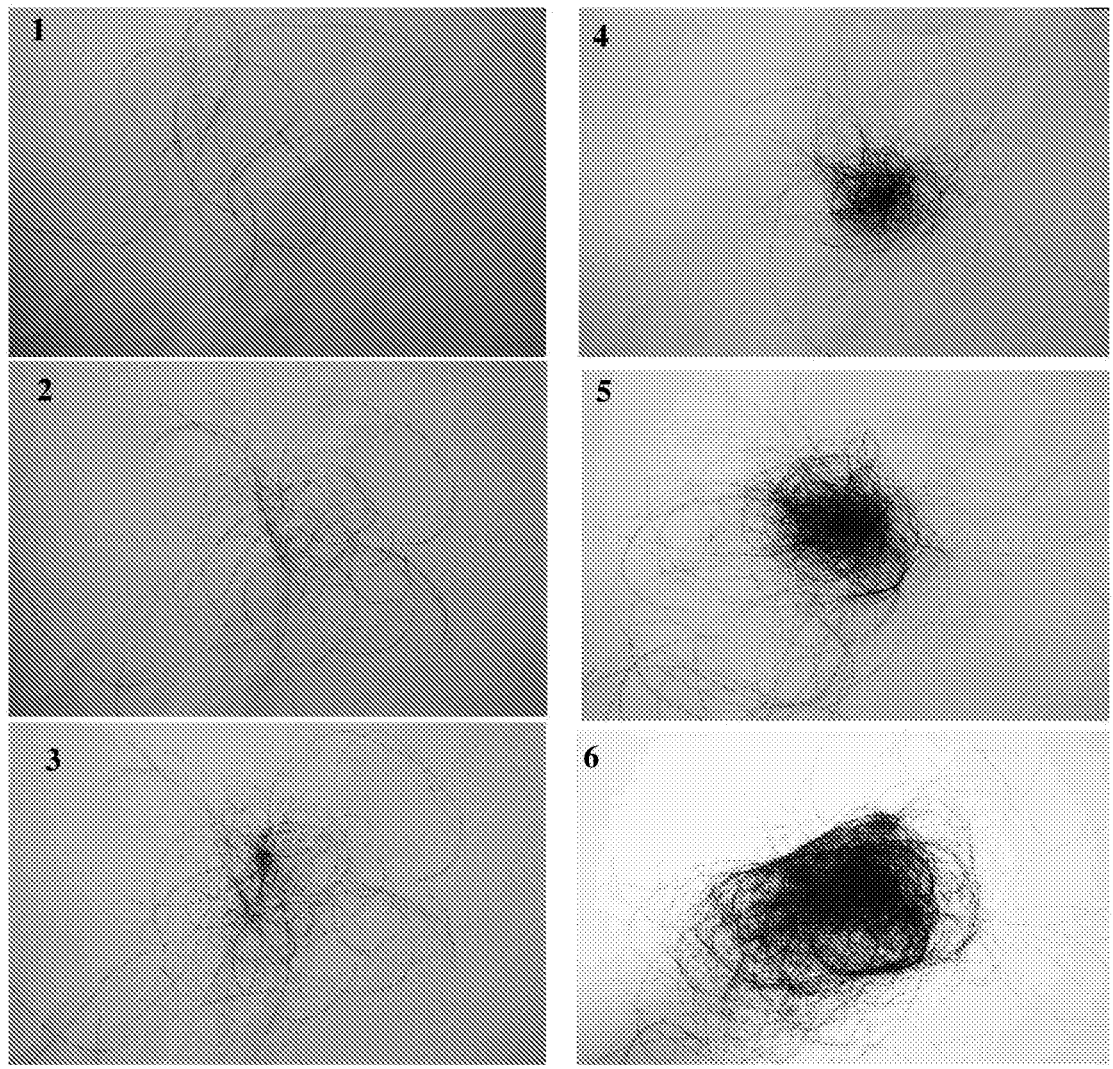
FIG. 1: Shows an embodiment of the visual analogue scale for the assessment of hair loss or excessive hair shedding. Images number 1 to 4 respectively represent bundles of 10, 50, 100 and 200 long hairs and are considered normal levels of hair shedding for women and girls with long hair. Images 5 and 6 show bundles of 400 and 750 long hairs and are considered excessive levels of hair shedding for women and girls with long hair. In this embodiment the visual analogue scale provides a hair shedding score (HSS) from 1 to 6.

As described herein, "minoxidil" is a piperidinopyrimidine derivative and a potent vasodilator (CAS ID: 38304-91-5). The term "minoxidil" is used in broad sense to include not only "minoxidil" per se but also its pharmaceutically acceptable derivatives thereof. Suitable derivatives include pharmaceutically acceptable salts, pharmaceutically acceptable solvates, pharmaceutically acceptable hydrates, pharmaceutically acceptable sulfates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc.

As described herein, "spironolactone" is an aldosterone antagonist and has been used as a potassium-sparing diuretic for over 50 years (CAS ID: 52-01-7). It is structurally a steroid, with basic steroid nuclei with four rings.

As described herein, "finasteride", also referred to as "propecia", is a type II 5α-reductase inhibitor, it acts by inhibiting the activity of 5α-reductase, an enzyme that converts testosterone to dihydrotestosterone (CAS ID: 98319-26-7). It is a synthetic drug for the treatment of benign prostatic hyperplasia and male pattern baldness and can be administered orally.

As described herein, "dutasteride" is a is a 5-α reductase inhibitor that inhibits conversion of testosterone to dihydrotestosterone (CAS ID: 164656-23-9).

As described herein, "flutamide" is an oral, non-steroidal antiandrogen drug (CAS ID: 13311-84-7).

As described herein, "cyproterone" is an oral steroidal antiandrogen (CAS ID: 2098-66-0).

As described herein, "bicalutamide" is an oral non-steroidal antiandrogen drug (CAS ID: 90357-06-5).

As described herein, "enzolutamide" is an oral non-steroidal antiandrogen drug (CAS ID: 90357-06-5).

As described herein, "nilutamide" is an oral non-steroidal antiandrogen drug (CAS ID: 90357-06-5).

As described herein, "apalutamide" is an oral non-steroidal antiandrogen drug (CAS ID: 90357-06-5).

As described herein, "buserilin" is an oral non-steroidal antiandrogen drug (CAS ID: 90357-06-5).

As described herein, "saw palmetto" is an oral non-steroidal antiandrogen drug (CAS ID: 90357-06-5).

As described herein, "azeleic acid" is an oral non-steroidal antiandrogen drug (CAS ID: 90357-06-5).

As described herein, "buserilin" is an oral non-steroidal antiandrogen drug (CAS ID: 90357-06-5).

As used herein the term "subject" refers to a mammal, particularly human. In one example the subject, is female.

As used herein, the terms "treating" or "treatment" of condition as used herein means: (1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms.

The methods described herein are relevant to the detection and/or treatment of "hair loss". One particular form of "hair loss" is "hair shedding" described as where hair falls out from skin areas where it is usually present, such as the scalp. Hair shedding can be described as either normal levels of hair shedding or excessive levels of hair shedding. The present disclosure provides a tool and method for characterizing hair loss as normal or excessive. Excessive hair loss or hair shedding may be a consequence of one of the following conditions: alopecia areata, androgenetic alopecia, telogen effluvium (chronic and acute), anagen effluvium, male pattern baldness, female pattern baldness, thyroid problems, monilethrix, anaemia, congenital hypotrichosis, short anagen syndrome, loose anagen syndrome, drug induced and chemotherapy induced hair loss, cicatricial alopecia (lichen planopilaris, discoid lupus erythematosus, folliculitis decalvans), congenital hypotrichosis, polycystic ovary syndrome or malnutrition. In one example, the condition is androgenic alopecia. In one example, the condition is telogen effluvium. In one example, the condition is chronic telogen effluvium. In one example, the condition is acute telogen effluvium. In one example, the subject is female. In one example, the subject is male.

As described herein, the composition is administered "orally", and is thus formulated in a form suitable for oral administration, i.e., as a solid or a liquid preparation. Suitable solid oral formulations include tablets, capsules, pills, granules, pellets, powders, and the like. Suitable liquid oral formulations include solutions, suspensions, dispersions, emulsions, foams, gels, oils and the like. In a preferred embodiment, the composition of this invention is a solid dosage form.

As described herein, the visual analogue scale can be used for assessing daily levels of hair loss or hair shedding. The visual analogue scale comprises a plurality of images on an individual page (or screen) or separate page (or screen) wherein each image displays a bundle of hair representative of a level of hair shedding. The visual analogue scale can comprise images representative of a normal level and/or an excessive level of hair shedding. Images may represent normal hair shedding levels, for example, (i) an image of a bundle of about 5 to 25 hairs; (ii) an image of a bundle of about 25 to 75 hairs; (iii) an image of a bundle of about 75 to 150 hairs; and/or may represent excessive hair shedding levels, for example, (i) an image of a bundle of about 300 to 750 hairs; (ii) an image of a bundle of about 500 to 1000 hairs. The visual analogue scale is suitable for at home use or use by a subject or in the clinical setting by clinicians. A subject or a clinician can use the scale to determine if the daily level of hair shedding is a normal or excessive level of hair shedding by visually determining if the amount of hair shed daily, or on an average day, corresponds to an image representative of normal or excessive daily hair shedding. The visual analogue scale can therefore be used daily, or on alternative days, or several days a week, or once a week or bi-weekly to assess hair shedding. Alternatively, the visual analogue scale may be used by a clinician to assess hair shedding at scheduled appointments for a subject. The visual analogue scale can be used to determine if hair shedding is increasing or decreasing in response to a particular treatment regimen and/or for the diagnosis of a hair loss condition. Additionally, the visual analogue scale may be used in combination with a questionnaire and or other diagnostics for diagnosing a hair loss or excessive hair shedding condition.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described examples, without departing from the broad general scope of the present disclosure. The present examples are, therefore, to be considered in all respects as illustrative and not restrictive.

The steps, features, integers, compositions and/or compounds disclosed herein or indicated in the specification of this application individually or collectively, and any and all combinations of two or more of said steps or features.

EXAMPLES

Example 1

Methods

Visual analogue scale: long, black/brown club hairs shed from a woman with FPHL was counted and separated into 6 bundles comprising 10, 50, 100, 200, 400 or 750 hairs. The bundles were photographed and were arranged order of size to develop a visual analogue scale shown in FIG. 1. The scale was piloted for usability as a hair loss assessment tool in a hair loss clinic. Test-test reliability was defined by scoring women again after 2 weeks. Hair shedding scores were subsequently obtained from women newly diagnosed with female pattern hair loss (FPHL). Normal shedding was defined among adolescent school girls.

In order to assess observer reliability of the hair shedding scale, 50 women attending a hair loss clinic for scalp biopsy were asked to look at an A4 page containing the 6 photos of hair bundles. The women were asked to point to the photograph that best correlates with the amount of hair that would be shed on a wash day, and which photo correlates best with the amount shed on a non-wash day. The frequency of hair washing was also recorded. The results were scored 1-6. When they returned 2 weeks later for removal of their sutures they were again shown the visual analogue scale and asked the same questions.

Female Pattern Hair Loss Group: Women newly diagnosed clinically with FPHL and/or histologically with androgenetic alopecia attending a specialist hair loss clinic were asked to score hair shedding using the visual analogue hair shedding scale. Women already taking oral antiandrogen treatment or using topical minoxidil were excluded. Only women with long or shoulder length hair were included.

Control group: As part of a school science project, 100 girls with straight long hair (below shoulder length) aged 11-15 years were shown the photographs and asked the same questions.

Results

Fifty women with FPHL were enrolled in the pilot study. Hair length was recorded as short, shoulder length or long. Scores at weeks 2 agreed with the scores at week 0 for 46 out of 50 women. Scores disagreed by 1 grade in 4 women. Of these four women all 4 had short hair. In all 4 cases where there was disagreement with the original score, the difference was only 1 grade. Two women increased their score and 2 women decreased their score. The correlation coefficient (r) was 0.98 and the coefficient of determination ($r^2$) was 0.96 indicating strong correlation (Table 1).

TABLE 1

| Hair Shedding Score | Assessment 1 | Assessment 2 |
|---|---|---|
| 1 | 2 | 2 |
| 2 | 3 | 3 |
| 3 | 6 | 7 |
| 4 | 10 | 10 |
| 5 | 13 | 13 |
| 6 | 16 | 17 |
| MEAN | 4.54 | 4.54 |
| Correlation Coefficient | | R = 0.98 |
| Coefficient of Determination | | $R^2$ = 0.96 |

As the photographs were bundles of long hair, and women with short hair had greater difficulty using the chart to score their hair shedding (and due to current fashion trends there were very few school girls to be found with short or shoulder length in the control group), FPHL patients with short or shoulder length hair were excluded from further analysis.

Female Pattern Hair Loss Group: Over a 52 week period scores were obtained from 209 consecutive women with previously untreated female pattern hair loss. The mean age was 46.3 years.

Among the 209 women with long hair, shedding was scored as: grade 6 in 93; grade 5 in 49; grade 4 in 40; grade 3 in 20; grade 2 in 6 and grade 1 in 1 woman. The mean shedding score was 4.93. Results are shown in Table 2.

Control Group: 100 school girls with a mean age of 13.51 years participated in the study. All had long hair. No girls with shoulder length or short hair were interviewed.

Scores are shown in Table 2. While androgenetic hair loss is reported in this age group, it is rare and this data was used as normal control. 99 girls had <grade 4 shedding. Only 1 girl had grade 5 shedding. No girl had grade 6 shedding. The mean hair shedding score was 2.68, which is significantly less than the mean shedding score seen in FPHL ($p<0.0001$).

TABLE 2

| Hair Shedding Score | 209 women with long hair and FPHL | 100 school girls with long hair and no FPHL |
| --- | --- | --- |
| 1 | 1 | 7 |
| 2 | 6 | 28 |
| 3 | 20 | 56 |
| 4 | 40 | 8 |
| 5 | 49 | 1 |
| 6 | 93 | 0 |
| MEAN | 4.93 (SD1.10) | 2.68 (SD0.76) |
| P value | | <0.0001 |
| Correlation Coefficient | $R = 0.98$ | |
| Coefficient of determination | $R^2 = 0.96$ | |

A visual analogue scale to assess female hair loss that is related to increased hair shedding is described. This tool was only studied in women and girls with long and shoulder length hair, as women in the pilot group with short hair found the scale difficult to use.

Data from the pilot study indicated that women can reliably self-score hair shedding.

Data form school girls with a mean age of 13.51 years, among whom androgenetic alopecia would be rare was used to define normal hair shedding as stages 1, 2, 3 or 4 for girls with long hair. Girls with short hair were not studied. Long hair is very much in fashion for adolescent school girls in Australia and girls with short hair are currently difficult to find.

A new visual analogue hair shedding scale accurately defines normal and abnormal hair shedding in females with long hair (FIG. 1). Grades 1-4 can be considered normal for women with long hair. Grades 5 and 6 shedding indicate excessive hair shedding in women. Excessive hair shedding is found in 68% of women with FPHL who have long hair.

Example 2

Assessment of the safety and effectiveness of a single once daily oral capsule containing minoxidil 0.25 mg and spironolactone 25 mg in the treatment of FPHL.
Methods Women with a Sinclair stage 2-5 female pattern hair loss were offered treatment with a single once daily capsule containing minoxidil 0.25 mg together with spironolactone 25 mg. For women with a baseline blood pressure <90/60 or a past history of postural hypertension or fainting 50 mg of sodium chloride was added to the capsule. Hair shedding was scored using a visual analogue scale (FIG. 1). Hair density was scored using the 5 stage Sinclair scale (Messenger et al. 2010). Women were reviewed at 3 monthly intervals. Blood pressure was recorded at each visit and patients were specifically questioned about the presence of unwanted facial or body hair at each follow-up visit and any other side-effects.

Full blood count, renal function, electrolytes and liver function testing was performed at baseline and at 3 monthly intervals.
Results 100 women with newly diagnosed Sinclair stage 2-5 female pattern hair loss were treated with a once daily capsule containing minoxidil 0.25 mg and spironolactone 25 mg and followed prospectively for 12 months.

The mean age was 48.44 years (range 18-80). Mean hair loss severity at baseline was Sinclair 2.79 (range 1-5). The mean hair shedding score at baseline was 4.82. Mean duration of diagnosis was 6.5 years (range 0.5-30).

Side effects were seen in 8 of women but were generally mild. No patients developed hyperkalaemia or any other blood test abnormality. Six of these women continued treatment and 2 women who developed urticaria discontinued treatment.

Baseline mean systolic blood pressure was 122.92 mmHg. Baseline mean diastolic pressure was 79.17 mmHg. Follow up blood pressure after 3 months was 118.40 systolic and 72.69 diastolic. Mean change in systolic blood pressure was −4.52 mmHg. Mean change in diastolic blood pressure was −6.48. Patients (2) developed symptoms of postural hypertension necessitating introduction of 50 mg daily of sodium chloride.

Four patients reported hypertrichosis. This was managed by a combination of plucking, or waxing.

A temporary increase in hair shedding 3-6 weeks following initiation of treatment was anticipated. Twenty-two patients reported this shedding as being of significant concern. All patients had been pre-warned about the possibility of a temporary increase in hair shedding on initiation of therapy and advised to continue treatment. No women discontinued the treatment as a result of increased hair shedding following commencement of therapy. For 16 women this shedding ceased within 4 weeks, while for 4 women it persisted for more 6 weeks and for 2 women it persisted for more than 12 weeks.

Two patients ceased the medication due to urticaria that was presumed to be related to the spironolactone. The urticaria settled within 7 days of cessation and did not recur when the minoxidil was recommenced as monotherapy.

Mean hair loss severity at baseline was Sinclair 2.79 (range 1-5). Mean hair shedding score at baseline was 4.82.

Figure 2:
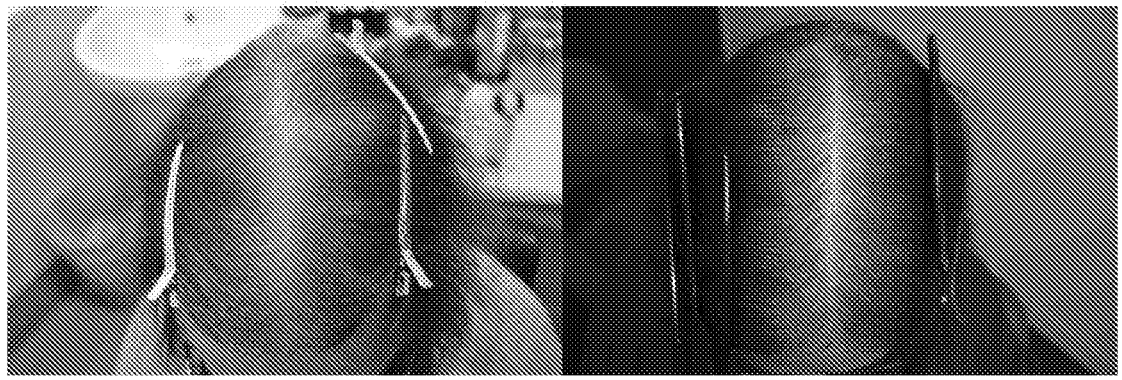
FIG. 2: Patients 1, 2, and 3 before (left) and after 12 months therapy (right).
Figure 2:
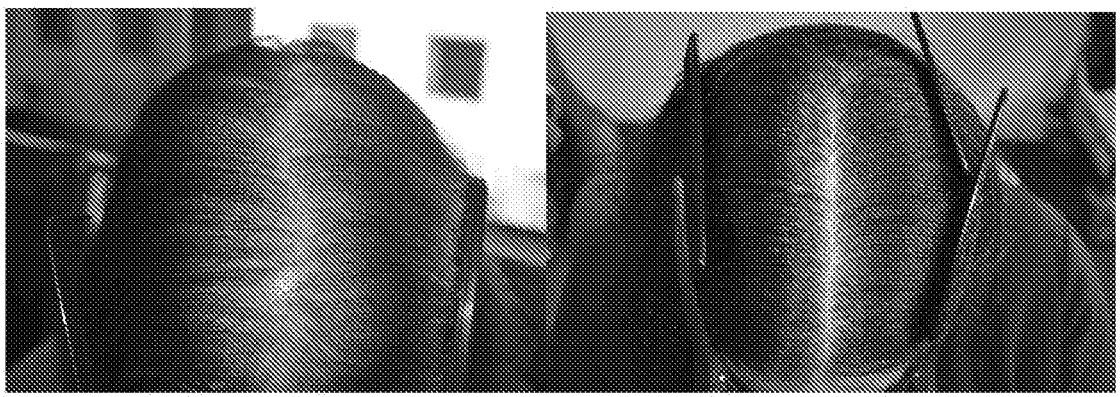
Figure 2:
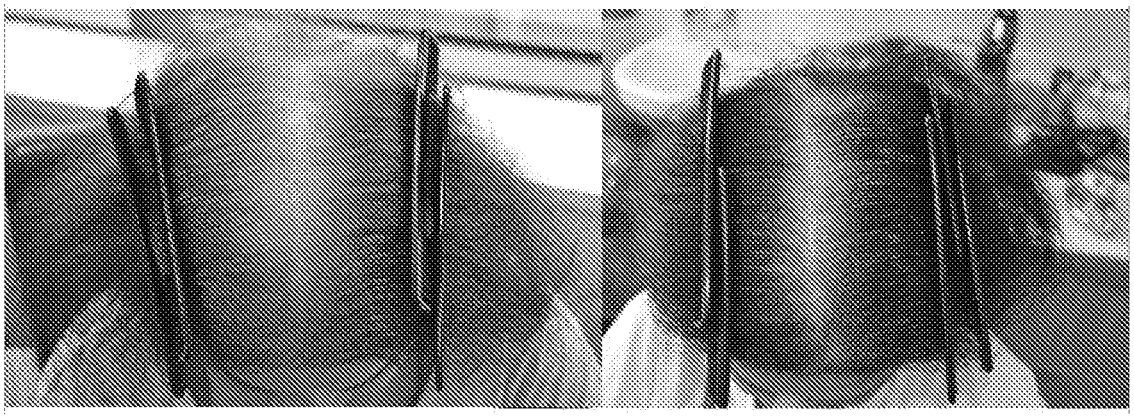
Figure 3:
FIG. 3: Patients 4 and 5 before (left) and after 12 months therapy (right).
Figure 3:

Mean reduction in hair loss severity score was 0.1 at 3 months, 0.85 at 6 months, 1.1 at 9 months and 1.3 at 12 months (FIGS. 2 and 3). Mean reduction in hair shedding score was 1.1 at 3 months, 2.3 at 6 months, 2.7 at 9 months and 2.6 at 12 months.

Once daily capsules containing minoxidil 0.25 mg and spironolactone 25 mg was well tolerated in the majority of patients with FPHL and is a reasonable alternative in women intolerant of, or unwilling to use topical minoxidil. While hyperkalaemia, creatinine elevation and hepatitis are reported with spironolactone, we did not encounter any haematological abnormalities at the dose used in this study.

Most women noticed a reduction in hair shedding at 3 months and an increase in hair density at 6 months.

Example 3

Monilethrix is an autosomal dominant genodermatosis characterized by hair fragility and breakage, keratosis pilaris and pathognomonic beading of the hair shaft. An autosomal recessive variant is also reported. There is no satisfactory treatment for Monilethrix. We report two cases of Monilethrix, where treatment with oral minoxidil led to a significant improvement in hair volume and length within three months.

The gene for autosome dominant monilethrix has been mapped to the epithelial keratin gene cluster on 12q13, (Ven Steensel et al. 2005) and point mutations has been found in the hair cortex-specific keratin genes KRT86, KRT83 and KRT81 (Horev et al. 2003; De Cruz et al. 2012). Mutations in desmoglein 4 is responsible for autosomal recessive variant of monilethrix. Monilethrix demonstrates considerable inter- and intra-familial variations in age of onset, severity, and natural history (De Cruz et al. 2012). Most often, hair is normal at birth and is progressively replaced by short, fragile, brittle hair during first months of life. Hair breakage secondary to hair fragility may be accompanied by follicular keratosis most commonly on the occiput. Eyebrows, eyelashes, pubic, axillary and general body hair may be affected along with the scalp.

In most patients, the hair loss persists with little change throughout life. Spontaneous improvement or complete recovery has been reported during pregnancy. There is no curative treatment for monilethrix. Reduction in hairdressing trauma may diminish weathering and improve severely affected cases (Sinclair and De Berker 1997).

Methods

Patient 6: A 40 year old woman presented with lifelong fragile, sparse, and thin hair. She had been diagnosed with monilethrix in childhood and presented seeking treatment for her hair. She reported striking improvement in hair volume and length during each pregnancy; that relapsed twelve months post-partum. Comorbidities included Crohn's disease and impaired hearing. Her daughter and two sons had also been diagnosed with monilethrix and suffered from sparse and fragile hair. On examination, she had brittle, lustreless, fragile short hair all over the scalp. Her hair crumbled when rolled between our fingers. She was noted to have small keratotic papules on the nape of the neck. There were no nail or tooth abnormalities detected. Dermoscopy (FIG. 4) confirmed the diagnosis of Monilethrix. As the application of topical minoxidil could potentially accentuate breakage of fragile hairs, treatment was commenced with oral minoxidil 0.25 mg daily.

Figure 4:
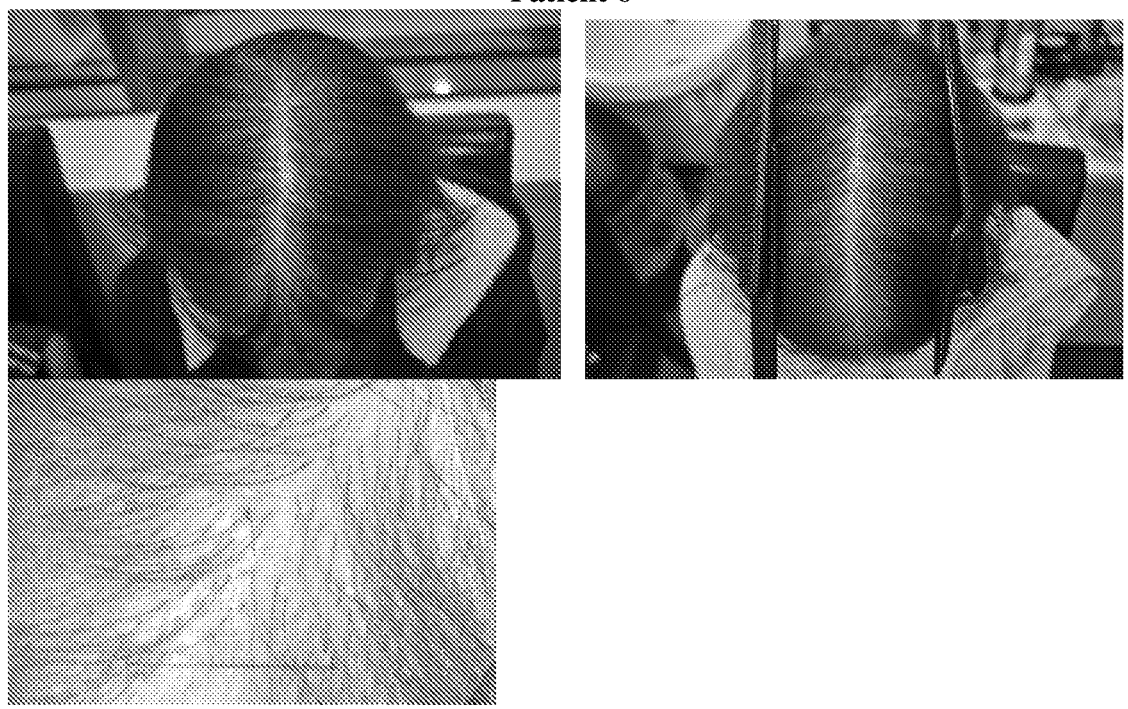
FIG. 4: Patient 6 before (left) and after 3 months therapy (right) and a dermoscopy confirming the diagnosis of monilethrix. Patient 7 before (above) and after (below images) therapy.
Figure 4:

Patient 7: A 35 year old woman with fragile, thin and sparse hair since childhood secondary to monilethrix presented for assessment and treatment. She had a positive family history of monilethrix affecting her son, daughter and grandson. Examination revealed brittle lustreless, fragile short hair all over the scalp, keratotic papules on the occipital scalp and keratosis pilaris. No nail or dental abnormalities were present. Dermoscopy showed elliptical nodes which separated by narrower internodes (FIG. 4). As the application of topical minoxidil could potentially accentuate breakage of fragile hairs oral Minoxidil 0.25 mg daily was commenced.

Results

Patient 6: Review after six months revealed significant hair growth with reduced breakage and increased hair volume and length (FIG. 4). The patient did not experience any side effects or complication of the treatment.

Patient 7: On examination three months following the initial consultation, hair shedding decreased significantly. However, the hair density remained unchanged. Minoxidil increased to 0.5 mg daily. There was a significant improvement in hair density on review at 6 months (FIG. 4).

Oral minoxidil is a promising treatment for hair loss associated with Monilethrix. When used in low doses it appears to be well tolerated.

Example 4

Chronic telogen effluvium (CTE) may be primary or secondary to a variety of causes including drug reaction, nutritional deficiency and female pattern hair loss (FPHL). The objective of this study is to assess the treatment of CTE with once daily oral minoxidil.

Methods:

The goals of this study were to review the use of oral minoxidil in CTE with respect to the response to hair shedding and safety. Hair shedding was assessed by patient self-reported Hair shedding Scores (HSS) using the visual analogue scale as described in Example 1 and FIG. 1. Hair Shedding Scores (HSS) were on the scale of 1 to 6 (6 being the highest level of hair shedding). Patients included in this study were women with a diagnosis of CTE based on >6 month history of increased telogen hair shedding, a HSS of 4-6, no visible mid frontal scalp hair loss (Sinclair stage 1) and no hair follicle miniaturization on scalp biopsy.

Data pertaining to dosage of oral minoxidil, previous treatments including topical minoxidil use, blood pressure, side effects, hypertrichosis and trichodynia were collected for each patient. Patient-reported responses were based on a visual analogue scale HSS at each consultation. The HSS prior to starting oral minoxidil, and scores at 6 and 12 months were extracted for analysis. Patients were treated with a once daily oral minoxidil (0.5 to 2.5 mg).

Data were analysed using Matlab R2014b statistical software. Hair shedding scores at baseline, 6 and 12 months were analysed using the Wilcoxon rank sum test for pairwise comparisons. Differences in blood pressure at baseline and 6 months were also analysed using Wilcoxon rank sum test. Relationship between outcomes (HSS at six and 12 months) and individual patient specific variables including previous use of age, topical minoxidil, duration of disease, dosage and HSS at baseline were analysed using a generalised linear regression model.

Results

Figure 5:
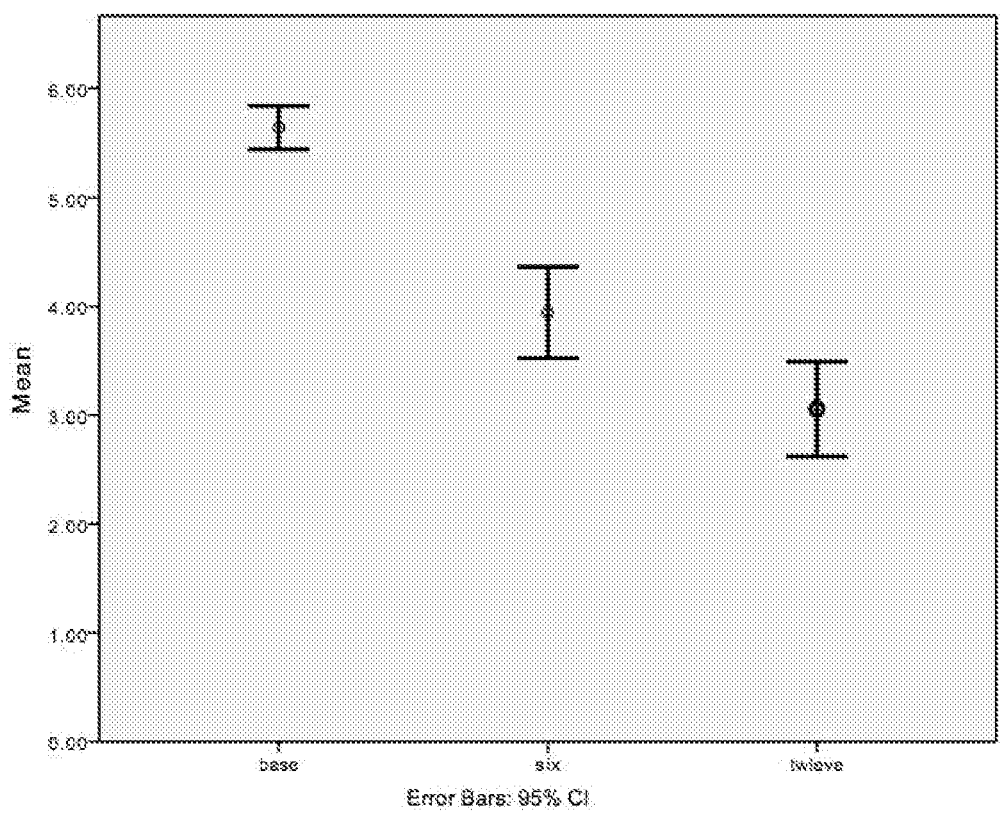
FIG. 5: Mean hair shedding score at baseline, six and twelve months of thirty-six women treated with oral minoxidil in doses ranging between 0.25 mg and 2.5 mg daily and for 6 months. Hair shedding was assessed with the visual analogue scale.

Thirty-six patients with CTE, who were prescribed oral minoxidil, were included in this analysis. The mean age was 46.9 years (range 21-83 years) and the dosage of oral minoxidil used varied between 0.5 and 2.5 mg with most patients being administered 1 mg. Mean baseline HSS was 5.63. Mean HSS improved at 6 and 12 months at 3.9 and 3.05 respectively (FIG. 5). There was a reduction in mean HSS from baseline to 6 months of 1.7 ($p<0.001$) and a reduction in mean HSS from baseline to 12 months of 2.58 ($p<0.001$). Similarly, a mean reduction of 0.89 in HSS was noted between 6 months and 12 months ($p=0.003$). Correlation between the duration of disease and previous topical minoxidil with HSS at 6 months ($R^2<0.22$) and 12 months ($R^2<0.11$) were weak. Eleven patients had previously used 5% topical minoxidil. Of these patients the mean change in the HSS was higher, although not statistically significant, compared to patients who did not use topical minoxidil. Mean reductions in HSS for patients who had previously used and not used topical minoxidil were 2 and 1.56 (p=0.22) at six months and 3.18 and 2.32 at 12 months (p=0.11). The HSS improved in 31 patients after 6 months; in 4 patients the HSS remained the same; and in 1 patient the score increased at the 6-month mark before improving, compared to baseline, at the 12-month mark. After 12 months the HSS remained equal or improved from baseline in all but 3 patients.

There were no significant differences between blood pressure at baseline and 6 months (p>0.05). The lowest blood pressure recorded was 90/70. All other patients in the study had a blood pressure above 100/70. Mean doses in patient groups based on the presence of side effects is presented in Table 3 (p-values represents significance of corresponding differences in doses). The 5 women who described trichodynia at baseline all noted improvement or resolution within 3 months. Mean change in blood pressure was minus 0.5 mmHg systolic and plus 2.1 mmHg diastolic. Two patients developed transient postural dizziness that resolved with continued treatment. One patient developed ankle oedema. Thirteen women developed facial hypertrichosis. For 6 women this was mild and did not required treatment. Four patients waxed their upper lip or forehead and three patients had laser hair removal. No patients developed any blood test abnormalities.

TABLE 3

|  | Yes | No | p-value |
|---|---|---|---|
| Hypertrichosis | 1.46 mg | 0.99 mg | 0.07 |
| Trichodynia | 1.19 mg | 1.11 mg | 0.75 |

All the patients in this study demonstrated an improvement at either the 6 month or 12 month mark, with 33 patients improved from baseline at the 12 month mark. This analysis of 36 patients from a single dermatology centre shows that low-dose oral Minoxidil may decrease hair shedding in women with CTE. Patients previously unresponsive to topical minoxidil may still benefit form oral minoxidil. The patient cohort experienced minimal side effects (dizziness and ankle swelling) which settled during the treatment.

Example 5

There are no FDA approved treatments for female pattern hair loss (FPHL). FPHL is the female equivalent of MPHL (Messenger et al. 2010). Female pattern hair loss most commonly affects the mid-frontal scalp (Olsen, 1999). A proportion of women with FPHL also have hair loss over the vertex scalp or bitemporal recession. Off label oral treatments for female pattern hair loss include the androgen receptor antagonists spironolactone, cyproterone acetate, flutamide as well as the 5 alpha reductase inhibitors finasteride and dutasteride (Messenger et al. 2010). While hair loss will be arrested in a proportion of women with these agents and regrowth over the vertex or mid-frontal scalp has been documented, regrowth of bitemporal hair loss is not reported with any of these agents (Messenger et al. 2010).
Methods:
Patients were treated for 6 weeks with oral minoxidil 0.25 mg daily.
Results
We report 2 women with significant bitemporal recession occurring in the context of female pattern hair loss who noticed bitemporal hair regrowth after 6 weeks of oral minoxidil 0.25 mg daily.

Figure 6:
FIG. 6: Patient 8 before (left) and after (right) therapy.

Patient 8: is a 45 year old woman who presented with a 2 year history of increased HSS (stage 6), reduction in the thickness of her ponytail by 50%, and loss of hair density over her vertex scalp and bitemporally. Her blood pressure was 110/70. She had baseline facial hypertrichosis, necessitating plucking her chin and upper lip one a month. Baseline blood tests were all normal. She was commenced on minoxidil 0.25 mg. On review at 3 months, the hair shedding had reduced to stage 5. Her blood pressure was 115/65. Her facial hypertrichosis was unaltered. He vertex hair density was slightly improved, while her bitemporal hair loss was noticeably improved (FIG. 6). In addition her hair was noted to be slightly darker in colour. She reported no side-effects from the treatment when questioned.

Figure 7:
FIG. 7: Patient 9 before (left) and after (right) treatment.

Patient 9: is a 48 year old woman who presented with a 3 year history of increased HSS (stage 6) mid-frontal hair loss (stage 3). Over that time she had noticed a reduction in the volume of her ponytail by over 50%. She had been commenced on spironolactone 200 mg daily by a local dermatologist 12 months prior. Her mid-frontal hair density had stabilized, but she continued to have increased hair shedding, trichodynia and bitemporal recession. Her Blood pressure was 140/85. Treatment was commenced on minoxidil 0.25 mg once daily. She continued to take the spironolactone, albeit in the reduced dose of 100 mg daily. Review at 6 weeks revealed a reduction in hair shedding (stage 4) and the trichodynia had disappeared after 2 weeks and not returned. While there was only slight improvement in her mid-frontal hair density at 6 weeks, there was significant bitemporal regrowth (FIG. 7). Her blood pressure was 125/85. All baseline haematological investigations were normal. She had not experienced any side effects or complications of treatment and in particular denied any facial hypertrichosis or unwanted hair elsewhere on the body.

This is the first report of treatment for bitemporal hair loss occurring in association with female pattern hair loss with an oral medication.

Example 6

Figure 8:
FIG. 8: Patient 10 before (left) and after (right) therapy. Patient 11 before (left) and after (right) treatment.
Figure 8:
Figure 9:
FIG. 9: Patient 12 before (left) and after (right) therapy. Patient 13 before (left) and after (right)
Figure 9:
Figure 10:
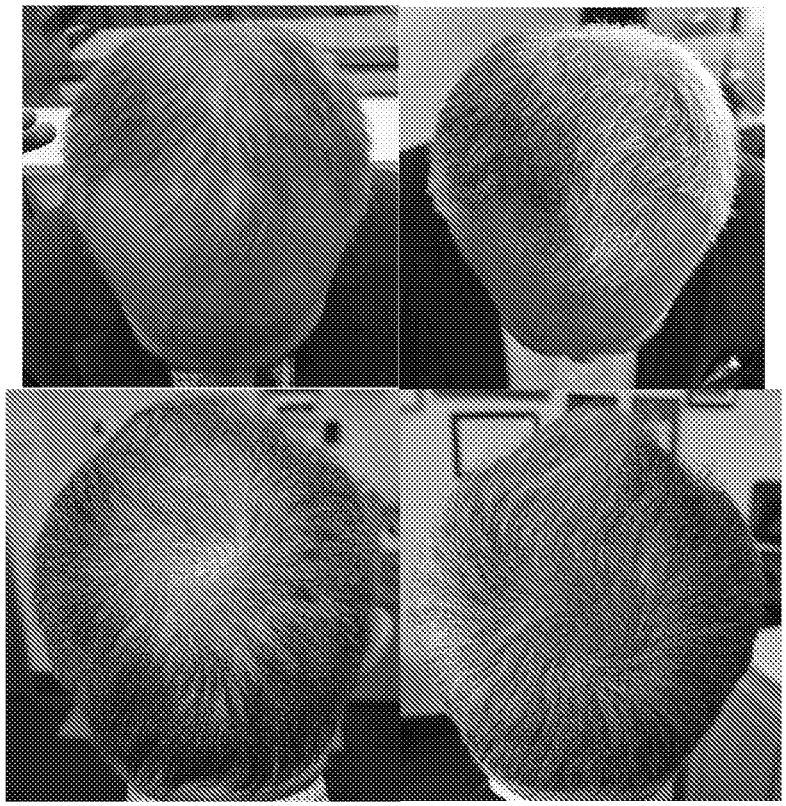
FIG. 10: Patient 14 before (left) and after (right) therapy. Patient 15 before (left) and after (right) treatment.
Figure 10:
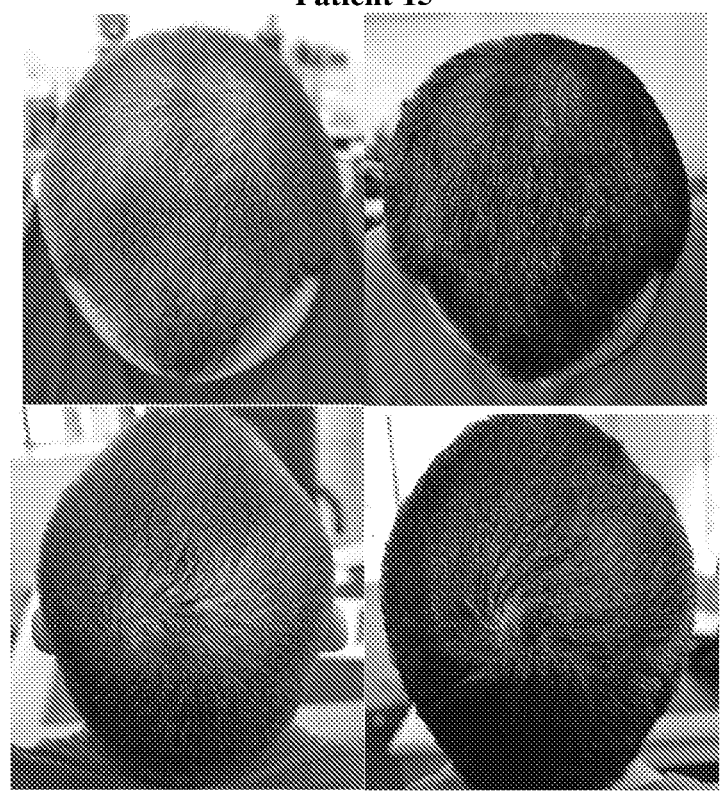

The objective of this study is to assess the impact of a single once daily dose of 0.25 mg oral minoxidil in AGA (androgenetic alopecia).
Methods
This study was a pilot, prospective, open, observational study conducted at the Sinclair Dermatology Clinic in Melbourne, Australia. Participants were dosed for 24 weeks. Treatment naïve men with Hamilton Norwood staged III vertex, IV or V were treated for 24 weeks with minoxidil 0.25 mg once daily. The primary efficacy endpoint was investigators' photographic assessment at week 24 and adverse events. Investigator photographic assessment was conducted by a single investigator grading the photographs using a 3 point rating scale, ranging from "decreased hair growth" to "increased hair growth," centred at no change. Any reports of adverse events were collected at every visit. Full blood count, renal function, electrolytes and liver function testing was performed at baseline and at 3 monthly intervals.
Results
Six men were treated with oral minoxidil 0.25 mg daily and for 6 months. Mean age was 50.17 years (range 23-65). All 6 completed 24 weeks of treatment. Global photographic assessment showed an increase in the hair at the anterior and vertex scalp in all 6 patients (the patients are numbered 10 to 15, images of before and after 24 weeks of treatment are shown in FIGS. 8 to 10). No adverse events were reported.

Low dose oral minoxidil 0.25 mg daily was well tolerated in all of our patients with MPHL.

REFERENCES

Bittencourt C, Ferraro D A, Soares T C, Moraes A M, Cintra M L. Chronic telogen effluvium and female pattern hair loss are separate and distinct forms of alopecia: a histomorphometric and immunohistochemical analysis. Clin Exp Dermatol 2014; 39:868-73.

Chong A, Wade M, Sinclair R. The hair pull test and the hair pluck test for the analysis of hair abnormalities. Modern Medicine (1999) 42: 105-108.

De Cruz R, Horev L, Green J, Babay S, Sladden M, Zlotogorski A, and Sinclair R. A novel monilethrix mutation in coil 2A of KRT86 causing autosomal dominant monilethrix with incomplete penetrance. British Journal of Dermatology (2012) 166:2 20-26.

Garcia-Hernandez M J, Camacho F M. Chronic telogen effluvium: incidence, clinical and biochemical features, and treatment. Arch Dermatol. 1999; 135:1123-4.

Harrison S, Sinclair R. Telogen effluvium. Clin Exper Dermatol. 2002; 27:389-5.

Horey L, Djabali K, Green J, Sinclair R, Martinez-Mir A, Ingber A, Christiano A M and Zlotogorski A. De novo mutations in monilethrix. Experimental dermatology (2003) 12:6 882-885.

Kıvanç-Altunay, İ., Savaş, C., Gökdemir, G., Köşlü, A., & Ayaydin, E. B. The presence of trichodynia in patients with telogen effluvium and androgenetic alopecia. Int Dermatol. 2003; 42, 691-693.

Messenger A G, Sinclair R D. Follicular miniaturization in female pattern hair loss: clinicopathological correlations. Br J Dermatol (2006) 155: 926-930.

Messenger A, De Berker D, Sinclair R. Disorders of Hair. In: Burns, Breathnach, Cox and Griffiths. Rook's Textbook of Dermatology. Eighth Edition. Blackwell Publishing. Oxford. (2010) 63.1-63.100.

Olsen, Elise A. The midline part: an important physical clue to the clinical diagnosis of androgenetic alopecia in women. Journal of the American Academy of Dermatology 40.1 (1999): 106-109.

Sinclair R, and D. De Berker. Hereditary and congenital alopecia and hypotrichosis. Diseases of the Scalp and Hair. R Dawber Editores. Blackwell Science. Oxford. Inglaterra (1997) 151-238.

Sinclair, R. "Chronic telogen effluvium or early androgenetic alopecia?." International journal of dermatology 2004; 43: 842-843.

Van Steensel, M A M, Steijlen P M, Bladergroen R S, Vermeer M, and van Geel M. A missense mutation in the type II hair keratin hHb3 is associated with monilethrix. Journal of medical genetics (2005) 42:3:e19-e19.

Whiting, David A. "Chronic telogen effluvium." Dermatol Clin 14.4 (1996): 723-731.

The invention claimed is:

1. A method of treating alopecia areata in a subject by administering to a subject an oral dose of minoxidil within the range from about 0.1 mg to 2.5 mg daily.

2. The method according to claim 1, which further comprises administering a: aldosterone antagonist, 5α-reductase inhibitor, non-steroidal antiandrogen drug and/or a steroidal antiandrogen.

3. The method according to claim 1, which further comprises administering spironolactone within the range of from about 10 mg to 500 mg.

4. The method according to claim 3, wherein spironolactone is at a concentration of about 25 mg.

5. The method according to claim 1, which further comprises administering sodium chloride with the range of from about 10 mg to 200 mg.

6. The method according to claim 5, wherein sodium chloride is at a concentration of about 20 mg.

7. The method according to claim 1, which additionally comprises administering one or more of:
   (i) finasteride within the range of from about 0.1 mg to 1 mg;
   (ii) dutasteride within the range of from about 0.01 mg to 1 mg;
   (iii) flutamide within the range of from about 10 mg to 500 mg;
   (iv) cyproterone acetate within the range of from about 1 mg to 100 mg;
   (v) bicalutamide within the range of from about 1 mg to 100 mg;
   (vi) enzalutamide within the range of from about 1 mg to 100 mg;
   (vii) nilutamide within the range of from about 1 mg to 100 mg;
   (viii) drosperidone within the range of from about 0.1 mg to 10 mg;
   (ix) apalutamide within the range of from about 1 mg to 100 mg; and
   (x) buseralin within the range of from about 0.1 mg to 10 mg.

8. The method according to claim 1, wherein the oral minoxidil dose is about 0.25 mg daily.

9. The method according to claim 8, which additionally comprises administering one or more of:
   (i) finasteride within the range of from about 0.1 mg to 1 mg;
   (ii) dutasteride within the range of from about 0.01 mg to 1 mg;
   (iii) flutamide within the range of from about 10 mg to 500 mg;
   (iv) cyproterone acetate within the range of from about 1 mg to 100 mg;
   (v) bicalutamide within the range of from about 1 mg to 100 mg;
   (vi) enzalutamide within the range of from about 1 mg to 100 mg;
   (vii) nilutamide within the range of from about 1 mg to 100 mg;
   (viii) drosperidone within the range of from about 0.1 mg to 10 mg;
   (ix) apalutamide within the range of from about 1 mg to 100 mg; and
   (x) buseralin within the range of from about 0.1 mg to 10 mg.

10. The method according to claim 1, wherein the oral minoxidil dose is about 2.5 mg, or is about 1 mg, or is about 0.5 mg, or is about 0.25 mg daily.

11. The method according to claim 10, which additionally comprises administering one or more of:
   (i) finasteride within the range of from about 0.1 mg to 1 mg;
   (ii) dutasteride within the range of from about 0.01 mg to 1 mg;
   (iii) flutamide within the range of from about 10 mg to 500 mg;
   (iv) cyproterone acetate within the range of from about 1 mg to 100 mg;

(v) bicalutamide within the range of from about 1 mg to 100 mg;
(vi) enzalutamide within the range of from about 1 mg to 100 mg;
(vii) nilutamide within the range of from about 1 mg to 100 mg;
(viii) drosperidone within the range of from about 0.1 mg to 10 mg;
(ix) apalutamide within the range of from about 1 mg to 100 mg; and
(x) buseralin within the range of from about 0.1 mg to 10 mg.

12. The method according to claim 1, wherein the oral minoxidil dose is about 2.5 mg daily.

13. The method according to claim 12, which additionally comprises administering one or more of:
(i) finasteride within the range of from about 0.1 mg to 1 mg;
(ii) dutasteride within the range of from about 0.01 mg to 1 mg;
(iii) flutamide within the range of from about 10 mg to 500 mg;
(iv) cyproterone acetate within the range of from about 1 mg to 100 mg;
(v) bicalutamide within the range of from about 1 mg to 100 mg;
(vi) enzalutamide within the range of from about 1 mg to 100 mg;
(vii) nilutamide within the range of from about 1 mg to 100 mg;
(viii) drosperidone within the range of from about 0.1 mg to 10 mg;
(ix) apalutamide within the range of from about 1 mg to 100 mg; and
(x) buseralin within the range of from about 0.1 mg to 10 mg.

14. The method according to claim 1, wherein the oral minoxidil dose is about 2 mg daily.

15. The method according to claim 14, which additionally comprises administering one or more of:
(i) finasteride within the range of from about 0.1 mg to 1 mg;
(ii) dutasteride within the range of from about 0.01 mg to 1 mg;
(iii) flutamide within the range of from about 10 mg to 500 mg;
(iv) cyproterone acetate within the range of from about 1 mg to 100 mg;
(v) bicalutamide within the range of from about 1 mg to 100 mg;
(vi) enzalutamide within the range of from about 1 mg to 100 mg;
(vii) nilutamide within the range of from about 1 mg to 100 mg;
(viii) drosperidone within the range of from about 0.1 mg to 10 mg;
(ix) apalutamide within the range of from about 1 mg to 100 mg; and
(x) buseralin within the range of from about 0.1 mg to 10 mg.

16. The method according to claim 1, wherein the oral minoxidil dose is about 1.5 mg daily.

17. The method according to claim 16, which additionally comprises administering one or more of:
(i) finasteride within the range of from about 0.1 mg to 1 mg;
(ii) dutasteride within the range of from about 0.01 mg to 1 mg;
(iii) flutamide within the range of from about 10 mg to 500 mg;
(iv) cyproterone acetate within the range of from about 1 mg to 100 mg;
(v) bicalutamide within the range of from about 1 mg to 100 mg;
(vi) enzalutamide within the range of from about 1 mg to 100 mg;
(vii) nilutamide within the range of from about 1 mg to 100 mg;
(viii) drosperidone within the range of from about 0.1 mg to 10 mg;
(ix) apalutamide within the range of from about 1 mg to 100 mg; and
(x) buseralin within the range of from about 0.1 mg to 10 mg.

18. The method according to claim 1, wherein the oral minoxidil dose is about 1 mg daily.

19. The method according to claim 18, which additionally comprises administering one or more of:
(i) finasteride within the range of from about 0.1 mg to 1 mg;
(ii) dutasteride within the range of from about 0.01 mg to 1 mg;
(iii) flutamide within the range of from about 10 mg to 500 mg;
(iv) cyproterone acetate within the range of from about 1 mg to 100 mg;
(v) bicalutamide within the range of from about 1 mg to 100 mg;
(vi) enzalutamide within the range of from about 1 mg to 100 mg;
(vii) nilutamide within the range of from about 1 mg to 100 mg;
(viii) drosperidone within the range of from about 0.1 mg to 10 mg;
(ix) apalutamide within the range of from about 1 mg to 100 mg; and
(x) buseralin within the range of from about 0.1 mg to 10 mg.

20. The method according to claim 1, wherein the oral minoxidil dose is about 0.75 mg daily.

21. The method according to claim 20, which additionally comprises administering one or more of:
(i) finasteride within the range of from about 0.1 mg to 1 mg;
(ii) dutasteride within the range of from about 0.01 mg to 1 mg;
(iii) flutamide within the range of from about 10 mg to 500 mg;
(iv) cyproterone acetate within the range of from about 1 mg to 100 mg;
(v) bicalutamide within the range of from about 1 mg to 100 mg;
(vi) enzalutamide within the range of from about 1 mg to 100 mg;
(vii) nilutamide within the range of from about 1 mg to 100 mg;
(viii) drosperidone within the range of from about 0.1 mg to 10 mg;
(ix) apalutamide within the range of from about 1 mg to 100 mg; and
(x) buseralin within the range of from about 0.1 mg to 10 mg.

22. The method according to claim 1, wherein the oral minoxidil dose is about 0.5 mg daily.

23. The method according to claim 22, which additionally comprises administering one or more of:
(i) finasteride within the range of from about 0.1 mg to 1 mg;
(ii) dutasteride within the range of from about 0.01 mg to 1 mg;
(iii) flutamide within the range of from about 10 mg to 500 mg;
(iv) cyproterone acetate within the range of from about 1 mg to 100 mg;
(v) bicalutamide within the range of from about 1 mg to 100 mg;
(vi) enzalutamide within the range of from about 1 mg to 100 mg;
(vii) nilutamide within the range of from about 1 mg to 100 mg;
(viii) drosperidone within the range of from about 0.1 mg to 10 mg;
(ix) apalutamide within the range of from about 1 mg to 100 mg; and
(x) buseralin within the range of from about 0.1 mg to 10 mg.

24. The method according to claim 1, wherein the oral minoxidil dose is about 0.49 mg, or is about 0.48 mg daily.

25. The method according to claim 24, which additionally comprises administering one or more of:
(i) finasteride within the range of from about 0.1 mg to 1 mg;
(ii) dutasteride within the range of from about 0.01 mg to 1 mg;
(iii) flutamide within the range of from about 10 mg to 500 mg;
(iv) cyproterone acetate within the range of from about 1 mg to 100 mg;
(v) bicalutamide within the range of from about 1 mg to 100 mg;
(vi) enzalutamide within the range of from about 1 mg to 100 mg;
(vii) nilutamide within the range of from about 1 mg to 100 mg;
(viii) drosperidone within the range of from about 0.1 mg to 10 mg;
(ix) apalutamide within the range of from about 1 mg to 100 mg; and
(x) buseralin within the range of from about 0.1 mg to 10 mg.

* * * * *